(12) United States Patent
Wasserman et al.

(10) Patent No.: US 8,005,523 B2
(45) Date of Patent: Aug. 23, 2011

(54) SIGNAL PROCESSING FOR PULSE OXIMETRY

(75) Inventors: Yoram Wasserman, Haifa (IL); Guy Russell Lowery, San Juan Capistrano, CA (US)

(73) Assignee: ConMed Corporation, Utica, NY (US)

( * ) Notice: Subject to any disclaimer, the term of this patent is extended or adjusted under 35 U.S.C. 154(b) by 1248 days.

(21) Appl. No.: 11/536,058

(22) Filed: Sep. 28, 2006

(65) Prior Publication Data

US 2007/0203417 A1  Aug. 30, 2007

Related U.S. Application Data

(60) Provisional application No. 60/722,257, filed on Sep. 30, 2005.

(51) Int. Cl.
*A61B 5/1455* (2006.01)
(52) U.S. Cl. .................. 600/323; 600/324; 600/336
(58) Field of Classification Search ................ 600/322, 600/323, 324, 336, 502
See application file for complete search history.

(56) References Cited

U.S. PATENT DOCUMENTS

| | | | |
|---|---|---|---|
| 4,193,393 A * | 3/1980 | Schlager | 600/523 |
| 4,960,126 A * | 10/1990 | Conlon et al. | 600/336 |
| 6,002,952 A | 12/1999 | Diab et al. | |
| 6,650,918 B2 | 11/2003 | Terry | |
| 6,684,090 B2 | 1/2004 | Ali et al. | |
| 6,816,741 B2 * | 11/2004 | Diab | 600/324 |
| 6,997,880 B2 * | 2/2006 | Carlebach et al. | 600/529 |
| 7,341,560 B2 * | 3/2008 | Henderson et al. | 600/500 |
| 2003/0055325 A1 | 3/2003 | Weber et al. | |

FOREIGN PATENT DOCUMENTS

| | | |
|---|---|---|
| EP | 1 297 784 | 4/2003 |
| WO | WO 2004/016169 | 2/2004 |
| WO | WO 2004/066161 | 8/2004 |

* cited by examiner

*Primary Examiner* — Eric F Winakur
*Assistant Examiner* — Chu Chuan Liu
(74) *Attorney, Agent, or Firm* — Timothy D Evans

(57) ABSTRACT

A signal processing technique for estimating the frequency of a pulsatile signal (including but not limited to pulse oximetry signals) is disclosed. Each of the functions contained within a pre-selected set of functions is compared to the input signal at many different time-shifts, and the function/time-shift combination that best matches the input signal is selected. The frequency of the best-matching function is then used as the best estimate of the frequency of the input signal. Optionally, once a function has been selected, the rising portion of the selected function can be correlated in time to the rising portion of the input signal. Improved results can then be obtained by basing the oxygen saturation level calculations on samples taken from the rising portion of the input signal.

13 Claims, 5 Drawing Sheets

SIGNAL PROCESSING FOR PULSE OXIMETRY

CROSS REFERENCE TO RELATED APPLICATIONS

This application claims the benefit of US provisional application No. 60/722,257, filed Sep. 30, 2005.

BACKGROUND

This application relates to determining the pulse rate of a biological pulsatile signal in the presence of noise. The techniques described herein are particularly useful for processing signals from pulse oximetry sensors.

Pulse oximetry is a non-invasive diagnostic procedure for measuring the level of oxygen saturation in a patient's arterial blood. Pulse oximetry is based on the principle of passing light energy from at least two wavelengths to a light-absorptive physiologic medium, acquiring the reflected (or transmitted) emitted light, in response to the light absorption, and calculating the oxygen saturation level from the acquired signals. Typical pulse oximeters have two main components: a sensor attached to a patient's skin for acquiring signals, and a processing unit for processing the acquired signals in order to determine the arterial blood oxygen saturation and pulse rate. Unfortunately, conventional pulse oximetry systems can be susceptible to noise, which can result in unstable readings, inaccurate measurements of pulse rate and oxygen saturation and false alarms. Noise can be particularly difficult to deal with in reflection pulse oximetry systems, where the signal levels are much smaller than in transmission pulse oximetry systems.

SUMMARY OF THE INVENTION

Each of the functions contained within a pre-selected set of functions is compared to the input signal at many different time-shifts, and the function/time-shift combination that best matches the input signal is selected. The frequency of the best-matching function is then used as the best estimate of the frequency of the input signal.

DETAILED DESCRIPTION OF THE PREFERRED EMBODIMENTS

While the preferred embodiments disclosed herein are described in the context of pulse oximetry, the present invention can be used in other contexts as well, including but not limited to signal processing for biological pulsatile signals obtained from sources other than oximetry probes.

To calculate the oxygen saturation level ($SpO_2$), from the acquired signals in a pulse oximetry system, it is often preferable to first determine the pulse rate of the signals and locate the pulse location. Obtaining an accurate estimation of the pulse rate and pulse location is important for calculating the correct oxygen saturation level in noisy signals.

Figure 1:
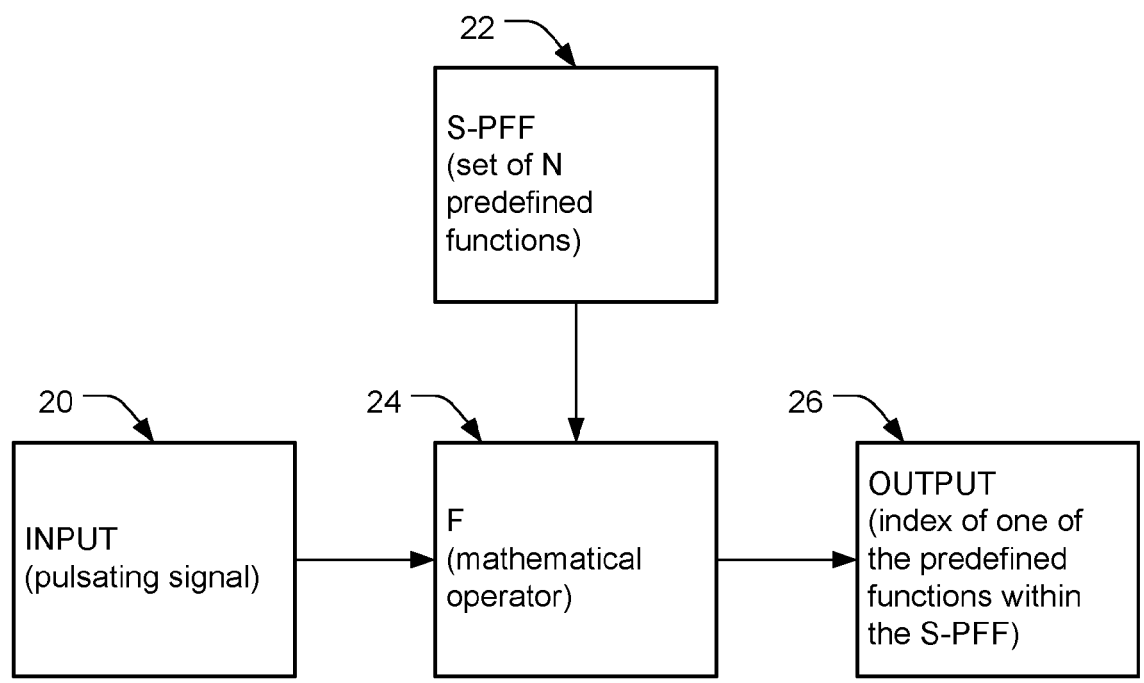
FIG. 1 is a block diagram depicting a method for determining the pulse rate of a pulsatile signal.

FIG. 1 is a block diagram of a preferred approach for determining the pulse rate of a pulsating input signal 20 by solving an optimization problem that involves a Set of Pre-Defined Frequency Functions (S-PFF). The pulsating input signal 20 and a S-PFF 22 enter a mathematical operator 24 for processing. The mathematical operator 24 is employed to transform a frequency estimation problem to an optimization problem. The output 26 of the system is the determined pulse rate for the input signal.

The input signal 20 may be the raw signal obtained from the source (e.g., the oximetry probe), or it may be a preprocessed. In one preferred embodiment, the DC and the very low frequency components of the input signal are removed by an appropriate preprocessing filter before entering the processing stage. Removing the DC component makes sure the processed signal pulsates around zero and has positive and negative peaks.

The S-PFF is a set of N periodic functions that is used in determining the frequency of the input signal. Preferably, the S-PFF functions are selected to resemble, at least roughly, the signals (with no noise added) that are expected in the desired application. The range of frequencies of the S-PFF functions, the number N of functions in a given S-PFF, and the size of the steps between successive frequencies are preferably selected based on the expected input signals and also based on the required accuracy of the obtained result. The advance selection of the functions contained within a given S-PFF may be accomplished using a suitable training process based on a data set that represents the signals that will be encountered during subsequent use.

Figure 2A:
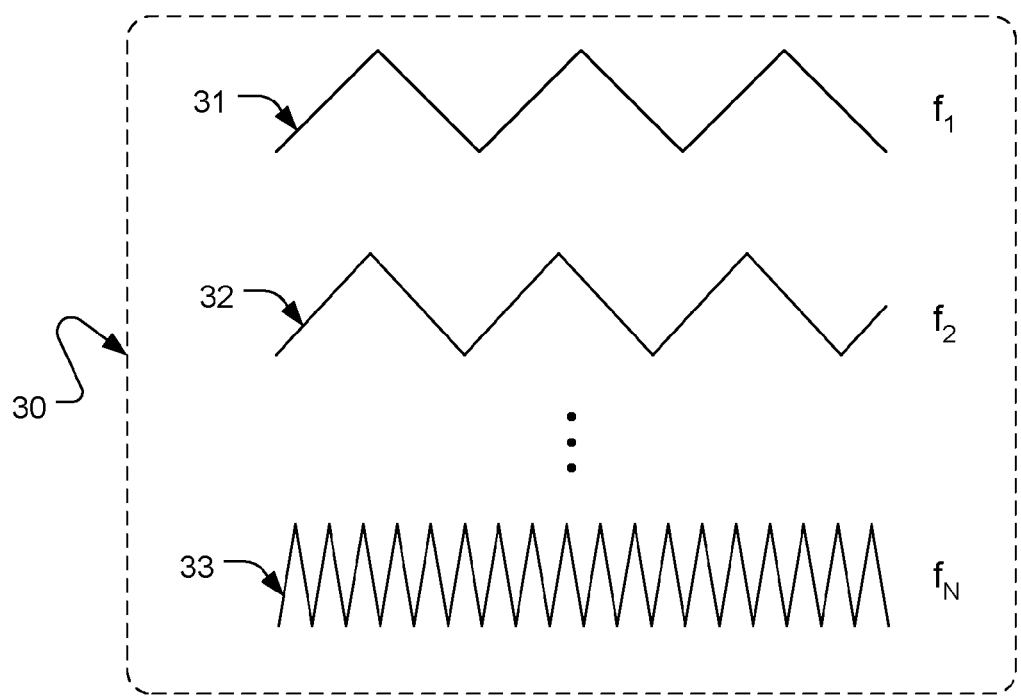
FIG. 2A is a first example of a Set of Pre-Defined Frequency Functions (S-PFF) for use with the method of FIG. 1.
Figure 2B:
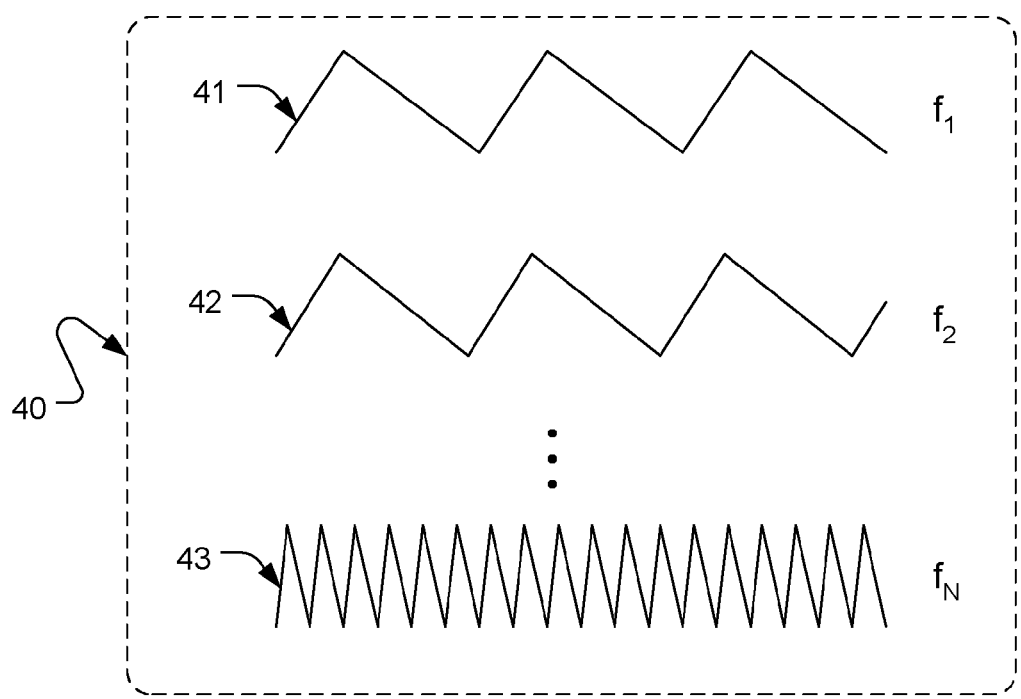
FIG. 2B is a second example of a S-PFF for use with the method of FIG. 1.
Figure 2C:
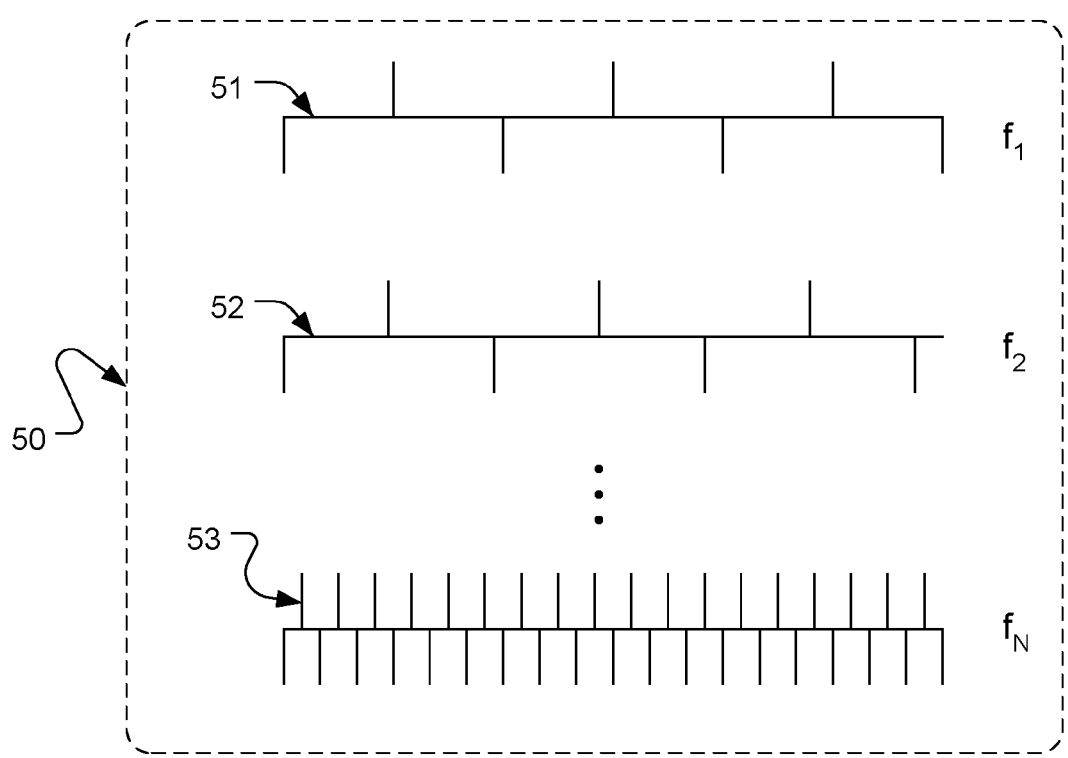
FIG. 2C is a third example of a S-PFF for use with the method of FIG. 1.

FIG. 2A is an example of a first S-PFF 30 that includes a set of N periodic waveforms 31-33, each having a similar symmetrical shape but with different frequencies $f_1$-$f_N$. FIG. 2B is an example of a second S-PFF 40 that includes a set of N periodic waveforms 41-43, each having a similar asymmetric shape but with different frequencies $f_1$-$f_N$. In alternative embodiments, a digital S-PFF 50 may be used, as shown in FIG. 2C. This third S-PFF 50 also includes a set of N periodic waveforms $f_1$-$f_N$ 51-53, each having a similar pattern but with different frequencies. In these embodiments, the functions 51-53 can take on only 3 values: $\{-1, 0, +1\}$. One advantage of using this type of S-PFF is that it makes performing mathematical operations simpler and faster, as compared to an analog S-PFF. It must be stressed that the S-PFFs 30, 40, 50 depicted in FIGS. 2A-C are merely examples of S-PFFs that may be used, and are not to be construed as limiting the present invention.

In the context of pulse oximetry, the input signal that is being processed is a physiological pulsating signal that originates from an optical sensor plus large amounts of noise. The rate of pulsation corresponds to the heart rate or pulse rate of the patient. Since the expected pulse rate for almost all patients will be between 30 and 240 beats per minute (bpm), an appropriate range of frequencies for an S-PFF used for pulse oximetry would be from ½ Hz (corresponding to 30 bpm) to 4 Hz (corresponding to 240 bpm). Since many medical applications require the heart rate to be determined with an accuracy and resolution of 1 bpm, an appropriate S-PFF for pulse oximetry would be a set 211 different frequencies (N=211) ranging from 30 bpm (½ Hz) to 240 bpm (4 Hz) in 1 bpm steps. If higher resolution or accuracy is desired, N can be increased beyond 211. Optionally, the steps between the various frequencies can be arranged nonlinearly with smaller bpm steps at lower frequencies and larger steps at the higher frequencies (e.g., in a logarithmic progression in order to achieve a uniform percentage accuracy).

In oximetry, the shape of the physiological pulsating signals in healthy patients will usually have a faster rise time and a slower fall time. As a result, one suitable S-PFF for pulse oximetry would be the S-PFF 40 shown in FIG. 2B, which also has a faster rise time and a slower fall time and therefore roughly matches the expected signal. As explained above, 211 frequencies (i.e., N=211) ranging from ½ Hz to 4 Hz in 1 bpm steps is an example of an appropriate distribution of frequencies for pulse oximetry applications. In some cases, however, the shape of the physiological pulsating waveform will differ (e.g., based on certain physiological conditions), which can give rise to degraded performance when the input waveform does not match up nicely to the waveforms in the S-PFF. It is therefore advantageous to incorporate a variety of different waveshapes within the S-PFF to account for such differences.

Figure 3:
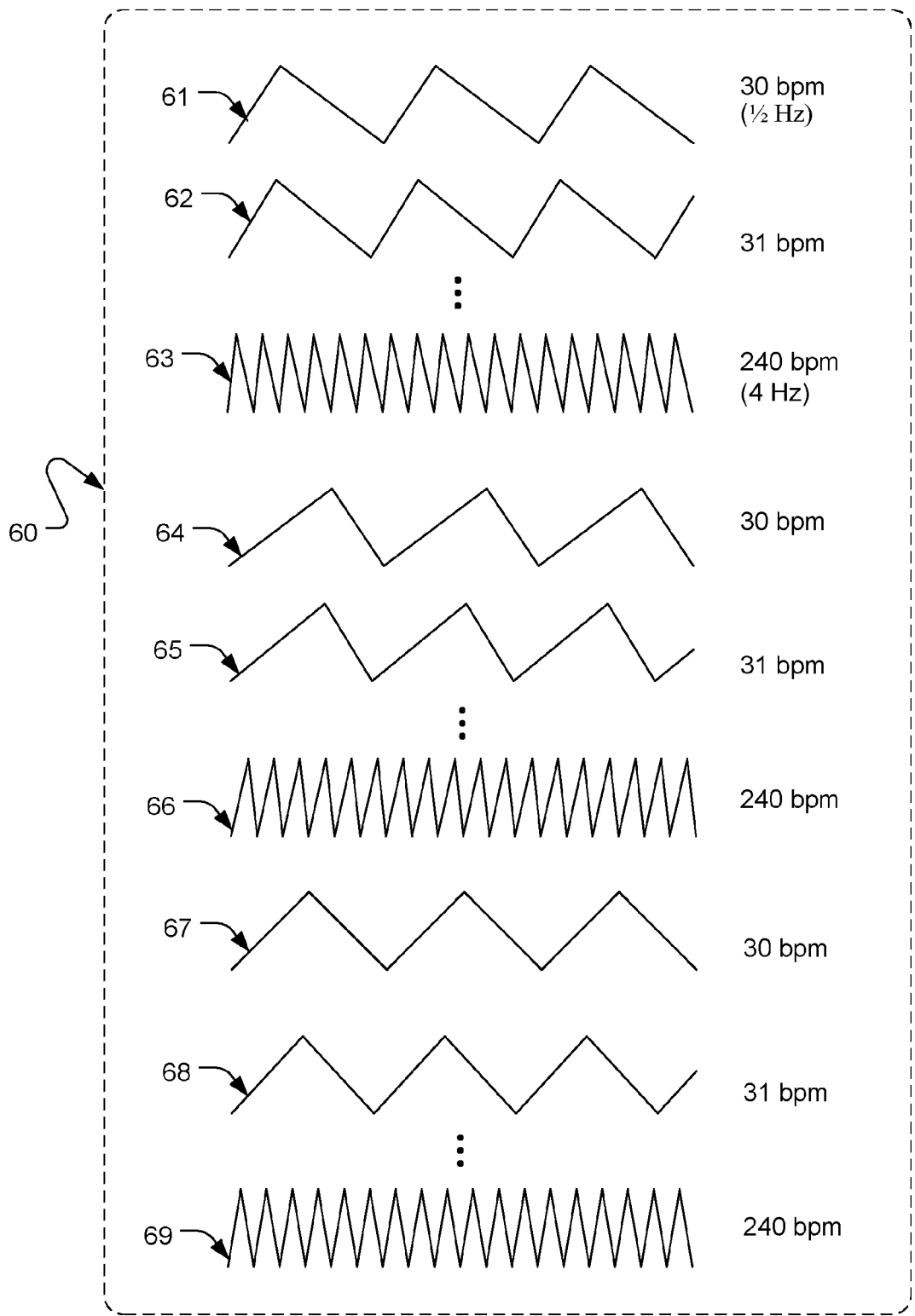
FIG. 3 is a fourth example of a S-PFF for use with the method of FIG. 1.

FIG. 3 is an example of a preferred S-PFF 60 for use in pulse oximetry applications that is optimized to handle input signals with different waveshapes. This S-PFF 60 includes one subset of functions 61-63 at 211 different frequencies ranging from 30 bpm to 240 bpm with faster rise times and a slower fall times, to match the expected physiological pulsating signals from most healthy patients. This S-PFF 60 also includes a second subset of functions 64-66 at each of the 211 different frequencies with slower rise times and a faster fall times, to match physiological pulsating signals with corresponding shapes from patients whose waveforms deviate from the more common fast-rising waveform. This S-PFF 60 also includes a third subset of functions 67-69 at each of the 211 different frequencies with matching rise times and fall times, to match physiological pulsating signals with corresponding shapes from patients whose waveforms deviate from the norm. Thus, the preferred S-PFF 60 contains a total of 633 functions (3×211). Note that a suitable duration for each of the functions 61-69 within the S-PFF 60 for use in pulse oximetry is 3-5 seconds long.

Another preferred S-PFF for use in pulse oximetry applications includes one subset of functions 61-63 at 211 different frequencies ranging from 30 bpm to 240 bpm with faster rise times and a slower fall times (to match the expected physiological pulsating signals from most healthy patients), and a second subset of functions 67-69 at each of the 211 different frequencies with matching rise times and fall times. This preferred S-PFF therefore contains a total of 422 functions (2×211). 3-5 seconds is also a suitable duration for each of the functions 61-63, 67-69 within this S-PFF.

Optionally, additional subsets of functions (not shown) may be added to match specific physiological conditions. For example, an additional set of 211 functions that match the physiological pulsating signals expected from patients with an incompetent mitral valve may be added to one of the S-PFFs discussed above. (The waveform expected from such patients differs from healthy patients because blood flow initially goes from the left ventricle into the left atrium. Only after sufficient pressure builds up does the aortic valve open.)

Optionally, different S-PFFs may be used for different classes of patients such as adults, children, babies, and fetuses. For example, the frequency range of the S-PFF may be shifted to higher frequencies for babies (as compared to the above-described range of 30-240 bpm).

Returning now to FIG. 1, the input signal 20 contains the underlying physiological pulsating signal plus noise. The input signal 20 and the S-PFF 22 enter a processing stage, which includes a mathematical operator F 24 that is designed to estimate the frequency of the input signal. The mathematical operator F converts the frequency estimation problem to an optimization problem, and its specific implementation depends on the application on hand. As in the case of the S-PFF, the mathematical operator F may be optimized and tested in a training session employed on a typical data set.

In one preferred embodiment of the invention, the mathematical operator F is defined as the following non linear operator:

$$F=\text{MAX}_{i,j}\{a_1 * f_1(\text{S-PFF}j(t), I(t-i))+a_2 * f_2(\text{S-PFF}j(t), I(t-i))+a_3 * f_3(\text{S-PFF}j(t), I(t-i))+a_n * f_n(\text{S-PFF}j(t), I(t-i))\} \quad (1)$$

Where:

$f_1$-$f_n$ are a set of n linear or non-linear functions;

S-PFF is a set of pre-defined frequency functions, as detailed above;

j is an index indicating a selected S-PFF function from the N S-PFF functions defined (note that n is independent of N);

$a_1$-$a_n$ are selected weighting constants;

\* is the multiplication operator;

I is the input signal;

t is an index indicating a specific sample of S-PFFj and I (i.e. these functions at time t); and i is a selected shift value, which indicates the current shift between the function S-PFFj and the input signal I.

The mathematical operator F represents an optimization problem, where a maximum is searched, as described by equation (1). In this way, each of the functions contained within the S-PFF is compared to the input signal at many different time-shifts, and the function/time-shift combination that best matches the input signal is selected (i.e., by selecting the combination where the maximum occurs). A suitable granularity for the time shift as between the various comparisons is a shift that corresponds to one sample. The frequency of the best-matching function is then used as the best estimate of the frequency of the input signal. For example, if in solving F the maximum was found at (j=12, i=5), this would indicate that S-PFF$_{12}$ is the function which provided the maximum result. Thus the frequency of function S-PFF$_{12}$ would be selected as the frequency of the input signal I for outputting. In the context of pulse oximetry, the frequency will be the pulse rate (i.e., the heart rate).

In addition to optimizing the S-PFF for the expected signals, as described above, the functions $f_1$-$f_n$ and weighting constants $a_1$-$a_n$, which are part of F may be defined and optimized at a training stage to best fit a specific application and the characteristics of the signals expected in that application. The optimization can be done using a suitable standard optimization method such as MLS (mean least squares) or maximum likelihood.

In one preferred embodiment that is suitable for determining the pulse rate in pulse oximetry systems using the preferred 633 function S-PFF 60 (shown in FIG. 3), n=3 so the mathematical operator F includes only three functions $f_1$, $f_2$ and $f_3$. In this embodiment, the function $f_1(i, j)$ is the sum of the products, obtained by multiplying the functions S-PFFj and input signal I, while shifted by i samples, and the weighting constant $a_1$ is +1, resulting in the following equation:

$$f_1(i,j) = \sum_t S\text{-}PFFj(t) * I(t-i).$$

The function $f_2(i, j)$ is the sum of differences between the consecutive values $I(t_k)$ of the input signal I and the weighting constant $a_2$ is $-1$. The values $\{t_k\}$ represent the indexes of the maxima of function S-PFFj(t). The function $f_3(i,j)$ is the sum of differences between the consecutive values $I(t_m)$, of the input signal and the weighting constant $a_3$ is also $-1$. The values $\{t_m\}$ represent the indexes of the minima of function S-PFFj(t). With this particular set of three functions, $f_1$ is mainly responsible for estimating the frequency or the pulse rate of the input signal. Functions $f_2$ and $f_3$ are mainly responsible for preventing the harmonic frequencies of the input signal from interfering with the frequency estimation.

Once the best function within the S-PFF is selected, the indexes $\{t_k\}$ represent the location of the maxima of the pulses while the indexes $\{t_m\}$ represent the location of the minima of the pulses. By subtracting the values of the acquired signals at the $\{t_m\}$ indexes from the values at the $\{t_k\}$ indexes, the amplitude of the pulses can be obtained. These values can be use for the calculation of the oxygen saturation level using standard oximetry methods.

Optionally, the pulse rate and/or the locations of the maxima and minima of the pulses may be used to pick a particular segment of the pulsatile wave for further processing. For example, in a pulse oximetry system, once the maxima, minima, and pulse rate are identified, the various phases of the cardiac cycle can be located (since the rising portion corresponds to the beginning of the cardiac cycle, and the declining portion corresponds to the end of the cardiac cycle). It turns out that improved results are obtained when samples that correspond to the rising portion are used for the $SpO_2$ calculations.

Figure 4:
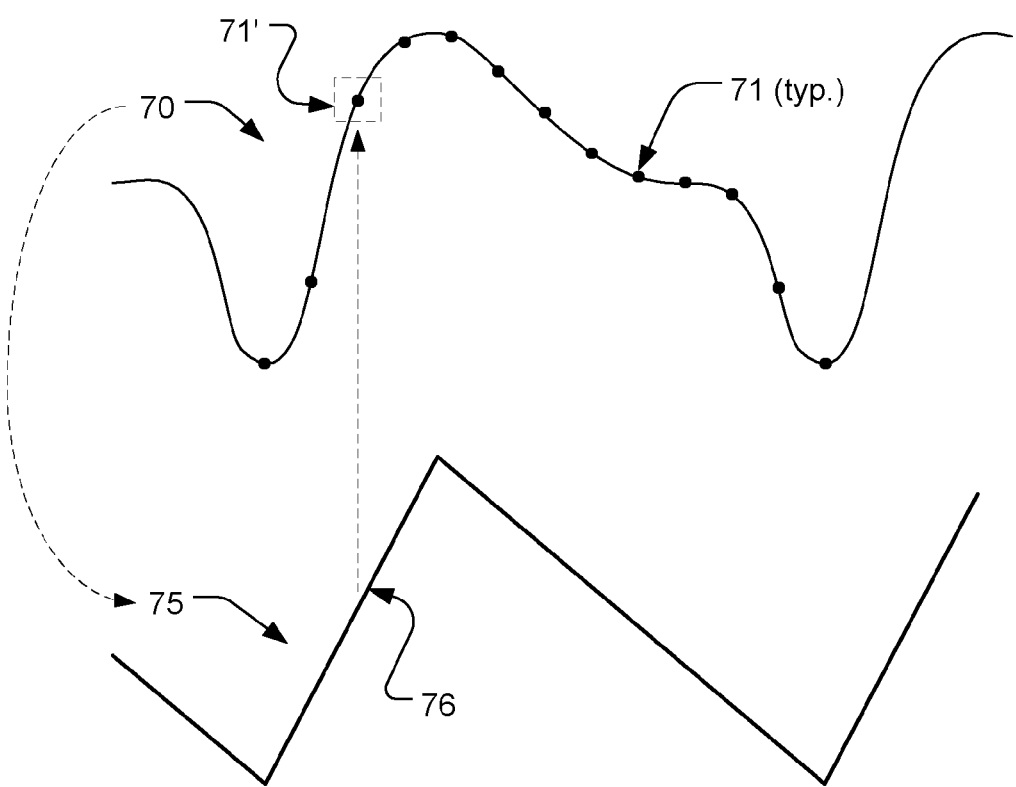
FIG. 4 shows an input signal and a matching function selected from the S-PFF

Turning now to FIG. 4, this approach may be extended further by taking a large number of samples during each cardiac cycle. In the illustrated example the incoming input signal 70 has a frequency of 1 Hz, which corresponds to 60 bpm, and has a relatively fast rising phase and a slower falling phase. By applying the signal processing techniques described above using the S-PFF 60 (shown in FIG. 3), the matching 60 bpm (1 Hz) function 75 should be selected as described above. If sampling is sufficiently fast to provide 12 $SpO_2$ measurements per second, overlaying the samples 71 of the input signal 70 onto the selected function 75 from the S-PFF enables differentiation between the various phases of the cardiac cycle. For example, samples on the rising phase of the input signal 70 can be identified by selecting the samples that correspond to the rising portion 76 of the selected function 75. In the illustrated example, sample 71' would be identified as corresponding to the rising portion of the input signal 70. That sample 71' would subsequently be used for making the $SpO_2$ calculations.

The above-describe embodiments provide an accurate and efficient approach for determine the frequency of a pulsatile input signal. This approach can successfully succeed in calculating the pulse rate even for very low SNR (Signal to Noise) values, which occur when the acquired reflected signal amplitude is low and the noise level is high. While the approach is described above in the context of determining the heart rate and the pulse locations from pulse oximetry derived signals, it should be recognized that these approaches may also be used to process other physiological pulsating signals. Moreover, the functions, frequency, resolution, duration, and frequency ranges set forth above are merely examples, and as such are not to be construed as limiting the present invention.

We claim:

1. A method of processing a pulse oximetry input signal, the method comprising the steps of:
   comparing the input signal at each of a plurality of different time shifts to each member of a set of functions, wherein the set includes functions with a plurality of different frequencies between 30 to 240 cycles per minute;
   selecting, based on results obtained in the comparing step, a function from the set that best matches the input signal;
   identifying a rising portion of the input signal based on an alignment in time with a rising portion of the selected function; and
   calculating an oxygen saturation level based on one or more samples taken from the portion of the input signal that was identified in the identifying step.

2. The method of claim 1, wherein the input signal has a sampling rate of at least 12 samples per second.

3. The method of claim 1, further comprising the step of removing DC and very low frequency components from the input signal, wherein the removing step is implemented before the comparing step.

4. The method of claim 1, wherein the functions in the set each have a duration between about 3 and about 5 seconds.

5. The method of claim 1, wherein the set contains at least 211 functions.

6. The method of claim 1, wherein the frequencies of the functions in the set are distributed in frequency to provide resolution of at least one cycle per minute.

7. The method of claim 1, wherein the set contains a first subset of functions in which the rise time is shorter than the fall time, and the shape of all the functions in the first subset is similar.

8. The method of claim 7, wherein the frequencies of the functions in the first subset are distributed in frequency to provide resolution of at least one cycle per minute.

9. The method of claim 7, wherein the set further contains a second subset of functions in which the rise time is about the same as the fall time, and the shape of all the functions in the second subset is similar.

10. The method of claim 9, wherein the frequencies of the functions in the first subset and the second subset are distributed in frequency to provide resolution of at least one cycle per minute.

11. The method of claim 10, wherein the set further contains a third subset of functions in which the rise time is longer than the fall time, and the shape of all the functions in the third subset is similar.

12. The method of claim 1, wherein the comparing and selecting steps are implemented based on the formula $$F = \text{MAX}_{i,j}\{a_1 * f_1(S\text{-}PFFj(t), I(t-i)) + a_2 * f_2(S\text{-}PFFj(t), I(t-i)) + a_3 * f_3(S\text{-}PFFj(t), I(t-i)) \ldots + a_n * f_n(S\text{-}PFFj(t), I(t-i))\},$$

where:
   $f_1$-$f_n$ are a set of n linear or non-linear functions;
   S-PFF is a set of pre-defined frequency functions;
   j is an index indicating a selected S-PFF function from the N S-PFF functions defined;
   $a_1$-$a_n$ are selected weighting constants;
   * is the multiplication operator;
   I is the input signal;
   t is an index indicating a specific sample of S-PFFj and I (i.e. these functions at time t); and
   i is a selected shift value, which indicates the current shift between the function S-PFFj and the input signal I.

13. The method of claim 1, wherein the comparing and selecting steps are implemented based on the formula $$F = \text{MAX}_{i,j}\{f_1(\text{S-PFF}j(t), I(t-i)) - f_2(\text{S-PFF}j(t), I(t-i)) - f_3(\text{S-PFF}j(t), I(t-i))\},$$

where:
the function $f_1(i, j)$ is the sum of the products, obtained by multiplying the functions S-PFFj and input signal I, while shifted by i samples, resulting in the equation $$f_1(i, j) = \sum_t S\text{-}PFFj(t) * I(t - i);$$

the function $f_2(i, j)$ is the sum of differences between the consecutive values $I(t_k)$ of the input signal I, where the values $\{t_k\}$ represent the indexes of the maxima of function S-PFFj(t);

the function $f_3(i, j)$ is the sum of differences between the consecutive values $I(t_m)$, of the input signal, where the values $\{t_m\}$ represent the indexes of the minima of function S-PFFj(t);

S-PFF is a set of pre-defined frequency functions;

j is an index indicating a selected S-PFF function from the N S-PFF functions defined;

I is the input signal;

t is an index indicating a specific sample of S-PFFj and I (i.e. these functions at time t); and i is a selected shift value, which indicates the current shift between the function S-PFFj and the input signal I.

* * * * *